(12) United States Patent
Weaver, II et al.

(10) Patent No.: US 10,369,038 B2
(45) Date of Patent: Aug. 6, 2019

(54) PLANTAR FASCIA SUPPORT SYSTEM

(71) Applicant: 3M INNOVATIVE PROPERTIES COMPANY, St. Paul, MN (US)

(72) Inventors: Edward L. Weaver, II, Milford, OH (US); Sherry A. Hinds, Goshen, OH (US); Beth E. Gramza, Cincinnati, OH (US)

(73) Assignee: 3M Innovative Properties Company, St. Paul, MN (US)

( * ) Notice: Subject to any disclaimer, the term of this patent is extended or adjusted under 35 U.S.C. 154(b) by 476 days.

(21) Appl. No.: 14/759,169

(22) PCT Filed: Jan. 7, 2014

(86) PCT No.: PCT/US2014/010485
§ 371 (c)(1),
(2) Date: Jul. 2, 2015

(87) PCT Pub. No.: WO2014/110029
PCT Pub. Date: Jul. 17, 2014

(65) Prior Publication Data
US 2015/0335460 A1 Nov. 26, 2015

Related U.S. Application Data

(60) Provisional application No. 61/750,278, filed on Jan. 8, 2013, provisional application No. 61/783,526, filed on Mar. 14, 2013.

(51) Int. Cl.
*A61F 5/01* (2006.01)
*A61F 5/05* (2006.01)
(Continued)

(52) U.S. Cl.
CPC ............ *A61F 5/0127* (2013.01); *A43B 7/141* (2013.01); *A43B 7/142* (2013.01); *A43B 7/143* (2013.01);
(Continued)

(58) Field of Classification Search
CPC .... A61F 5/0127; A61F 5/0111; A61F 5/0113; A61F 5/0195; A61F 5/019; A61F 5/01;
(Continued)

(56) References Cited

U.S. PATENT DOCUMENTS 1,538,026 A   5/1925  Cramer
1,785,185 A * 12/1930 Day ........................ A61F 5/019
                                                                 602/30
(Continued)

FOREIGN PATENT DOCUMENTS

GB         224718      11/1924
GB        2458282       9/2009
(Continued)

OTHER PUBLICATIONS

International Search report for PCT International Application No. PCT/US2014/010485 dated Mar. 27, 2014, 3 pages.

*Primary Examiner* — Alireza Nia
*Assistant Examiner* — Rachel A Berezik
(74) *Attorney, Agent, or Firm* — Ann Gallagher

(57) ABSTRACT

Low profile, contoured footplates that maintain tension in the plantar fascia without causing undue discomfort to the user are suggested for treatment of plantar fasciitis and other heel pain. The footplates may be ambidextrous and thus used to support either the left and right plantar fascia. The footplates can be used in assemblies for securing the footplate to the wearer's foot, as well as systems for iterative treatment of plantar fasciitis and other heel pain.

4 Claims, 6 Drawing Sheets

(51) Int. Cl.
  *A61F 5/14* (2006.01)
  *A43B 7/14* (2006.01)
(52) U.S. Cl.
  CPC .............. *A43B 7/1465* (2013.01); *A61F 5/01* (2013.01); *A61F 5/0111* (2013.01); *A61F 5/05* (2013.01); *A61F 5/14* (2013.01)
(58) Field of Classification Search
  CPC .... A61F 5/058; A61F 5/05825; A61F 5/0585; A61F 5/14; A61F 13/041; A61F 13/045; A61F 13/06; A61F 13/064; A61F 13/065; A61F 13/067; A43B 7/14; A43B 7/1405; A43B 7/141; A43B 7/142; A43B 7/143; A43B 7/1445; A43B 7/1465; A43B 7/1495; A43B 13/36
  See application file for complete search history.

(56) References Cited

U.S. PATENT DOCUMENTS

| | | | |
|---|---|---|---|
| 2,123,552 A | 7/1938 | Helwig | |
| 2,312,378 A | 3/1943 | Baum | |
| 4,686,994 A * | 8/1987 | Harr | A43B 7/142 36/145 |
| 5,399,155 A | 3/1995 | Strassburg | |
| 5,460,601 A | 10/1995 | Shannahan | |
| 5,554,107 A | 9/1996 | Shannahan | |
| 5,611,153 A | 3/1997 | Fisher | |
| 5,718,673 A | 2/1998 | Shipstead | |
| 5,840,053 A * | 11/1998 | Roth | A61F 5/0111 36/145 |
| 6,039,706 A * | 3/2000 | Bolla | A61F 5/05825 602/21 |
| D445,192 S | 7/2001 | Rodgers | |
| 6,315,786 B1 | 11/2001 | Smuckler | |
| 6,585,674 B2 * | 7/2003 | Toda | A61F 5/0111 128/876 |
| 6,886,276 B2 | 5/2005 | Hlavac | |
| 7,753,864 B2 | 7/2010 | Beckwith | |
| 7,856,742 B2 * | 12/2010 | Nguyen | A61F 5/14 36/155 |
| 7,958,653 B2 * | 6/2011 | Howlett | A43B 7/142 36/35 R |
| 8,162,868 B2 | 4/2012 | Llorens | |
| 8,240,066 B2 * | 8/2012 | Logan | A61F 5/0111 36/145 |
| 2002/0099317 A1 * | 7/2002 | Plotkin | A61F 5/14 602/66 |
| 2002/0178621 A1 * | 12/2002 | Darby | A43B 3/128 36/140 |
| 2003/0061736 A1 * | 4/2003 | Polifroni | A43B 7/14 36/44 |
| 2003/0145495 A1 | 8/2003 | Green | |
| 2004/0118020 A1 | 6/2004 | Hlavac | |
| 2004/0194348 A1 * | 10/2004 | Campbell | A43B 7/142 36/93 |
| 2005/0044751 A1 | 3/2005 | Alaimo et al. | |
| 2006/0161090 A1 | 7/2006 | Lee | |
| 2006/0288613 A1 | 12/2006 | Lo | |
| 2007/0283597 A1 | 12/2007 | Logan | |
| 2007/0289170 A1 * | 12/2007 | Avent | A61F 5/14 36/166 |
| 2008/0016724 A1 | 1/2008 | Hlavac | |
| 2008/0091131 A1 | 4/2008 | Caselnova | |
| 2009/0025254 A1 | 1/2009 | Smith | |
| 2009/0192428 A1 | 7/2009 | DeBoer | |
| 2009/0282699 A1 | 11/2009 | Labogin | |
| 2010/0018077 A1 | 1/2010 | Marone | |
| 2010/0146816 A1 | 6/2010 | Cappaert | |
| 2010/0249685 A1 | 9/2010 | Llorens | |
| 2014/0013618 A1 * | 1/2014 | Ruthven | A43B 7/144 36/44 |

FOREIGN PATENT DOCUMENTS

| | | |
|---|---|---|
| GB | 2464309 | 4/2010 |
| JP | 2009-125326 A | 6/2009 |
| WO | WO 1991-07152 | 5/1991 |
| WO | WO 2000-03615 | 1/2000 |
| WO | WO 2006/068513 | 6/2006 |
| WO | WO 2010-068719 | 6/2010 |
| WO | WO 2010-111618 | 9/2010 |

* cited by examiner

PLANTAR FASCIA SUPPORT SYSTEM

CROSS REFERENCE TO RELATED APPLICATIONS

This is a national stage filing under 35 U.S.C. 371 of PCT/US2014/010485, filed Jan. 7, 2014, which claims priority to U.S. Provisional Application No. 61/750,278, filed Jan. 8, 2013, and also claims priority to U.S. Provisional Application No. 61/783,526, filed Mar. 14, 2013, the disclosure of which is incorporated by reference in its/their entirety herein.

BACKGROUND

Plantar fasciitis is an inflammation of the plantar fascia near the point where it attaches to the front surface of the calcaneus or heel bone. The plantar fascia becomes broader and thinner as it extends longitudinally across the bottom of the foot, eventually dividing near the heads of the metatarsal bones into five processes, one for each of the five toes. The strongest ligament in the body, the plantar fascia's purpose is to protect the softer muscles and tissues of the bottom of the foot from injury, as well as to help maintain the integrity of the foot structure itself. If the fascia becomes stretched or strained, the arch area becomes tender and swollen as well as the area about the heel bone. This inflammation is called plantar fasciitis and is typically painful from the heel throughout the arch up into the Achilles tendon. Patients suffering from this condition usually have relatively tight and inflexible heel cords, sometimes referred to as Achilles tendon tightness. When the heel cord is tight, it causes compensation in the foot with over pronation of the foot during weight bearing. The pain is consistently worse when one first arises in the morning and at the end of the day. The pain usually lurks in the heel pad and may include the arch ligament. A common tendency is to ignore the symptoms of the pain at first.

Plantar fasciitis is often caused by contracture of the Achilles tendon and the plantar fascia, which can occur at night during sleep, or during daytime inactivity. The Achilles tendon, the strongest and thickest tendon in the human body, begins at or about the middle of the posterior side of the leg extending downward towards the heel, narrowing as it progresses towards its point of insertion at the posterior surface of the os calcis. When an individual is standing, walking, running, or even sitting in a position in which the feet are in contact with the floor or other surface, both the plantar fascia and the Achilles tendon are extended to varying degrees depending of course on the nature and intensity of the activity. During sleep, an individual has a natural tendency to plantarflex the ankle joint beyond the position which is normal during walking, standing, or sitting with one's feet on the floor. Plantarflexion occurs when the bottom of the foot is extended so as to form an angle with the lower leg of greater than 90°, i.e., extend such that the forefoot moves away from the body. Dorsiflexion is the opposite motion: when the foot is moved to a position in which the bottom of the foot forms an angle with the lower leg of less than 90°, i.e., such that the top of the foot moves toward the body.

Plantar fasciitis leads to pain on weight-bearing and tenderness to deep pressure over the plantar fascia at the heel-bone junction. Additional swelling and inflammation may develop. These conditions worsen with activity. Any activity which causes the foot to spread (e.g., prolonged standing) or which causes springing of the foot (e.g., running and jumping) can aggravate the condition.

Common methods of treatment of plantar fasciitis and Achilles tendonitis include night splints and orthotic inserts. A night splint typically consists, essentially, of a strap or boot-like structure that is strapped to a patient's lower leg and a means for holding the ankle joint in dorsiflexion. In so doing, both the plantar fascia and the Achilles tendon are slightly extended and are not allowed to contract during the night. Exemplary night splints are disclosed in U.S. Pat. No. 5,399,155 (Strassburg et al.), U.S. Pat. No. 5,718,673 (Shipstead), and U.S. Pat. No. 7,753,864 (Beckwith et al.).

As the name suggests, however, night splints do not allow a sufficient range of motion, flexion, or extension to be used consistently by ambulatory users during the day. A first class of devices for ambulatory use is similar to a night splint, boot-like in appearance, and maintains the shin to foot alignment of 90 degrees or potentially wedging the toes to keep the plantar fasciitis under tension. Other devices are typically inserted between the insole of a shoe and a user's foot and utilize gel and/or foam to provide heel padding to avoid shock and distributive force, purportedly alleviating the pain associated with plantar fasciitis. Exemplary insertable devices are disclosed in U.S. Pat. No. 5,611,153 (Fisher et al.), U.S. Pat. No. 6,315,786 (Smuckler) and U.S. Publication Nos. 2004/0194348 (Campbell et al.) and 2010/0146816 (Cappaert et al.). Additional treatment devices include elastic or inelastic textile wraps with padding applied circumferentially between the forefoot and the heel. Illustrative wrap devices are disclosed in U.S. Pat. No. 5,460,601 (Shannahan) and U.S. Pat. No. 6,886,276 (Hlavac). Other devices provide particularized support to the mid-foot and arch regions, such as the devices illustrated in U.S. Pat. No. 1,538,026 (Cramer), U.S. Pat. No. 4,686,994 (Harr et al.), U.S. Pat. No. 8,162,868 (Llorens et al.), and Campbell et al.

SUMMARY

The need exists for improved devices for treating plantar fasciitis, particularly during normal waking hours. The comprehensive, boot-like devices can be cumbersome, bulky and incompatible with certain footwear. User compliance with the rigid, bulkier products accordingly tends to be low. While it can be easier for a user to continually wear inserts or wraps, these devices generally allow the plantar fascia to cycle between flexion and extension while the wearer is ambulatory, not allowing the fascia to heal under a tensioned state. If subjected to this cycle of flexion and extension, the fascia can be susceptible to aggravation of micro-tears, potentially prolonging or exacerbating general heel/foot pain.

The present disclosure provides a low profile, contoured footplate that maintains tension in the plantar fascia without causing undue discomfort to the user. The footplate may be ambidextrous and may be used to support the plantar fascia in the left and right foot. The present disclosure further provides assemblies for securing the footplate to the wearer's foot, as well as systems for iterative treatment of plantar fasciitis and other heel pain. Unlike the aforementioned boot-like products, the footplates and plantar support assemblies of the present disclosure can be worn in conjunction with footwear, increasing the likelihood of compliance and repeated use. The present devices/assemblies/systems, unlike typical gel and/or foam products, provide targeted padding, shock resistance, and fascia tension. The plantar support assemblies of the present disclosure are particularly designed to conform to anatomical structures in the foot and promote comfort, thus allowing for dispersed pressure and higher distributed forces while mitigating pain or discomfort. The support assemblies and systems of the present disclosure functionally support the plantar fascia by maintaining flexion to avoid shortening of the fascia. This maintained position helps allow the micro-tears and/or inflammation to properly heal.

The plantar support systems and assemblies may be used in conjunction with a night time therapy product; in certain circumstances, the combined therapies enhance the effectiveness of the treatment and reduce the window of time that the wearer is afflicted by the pain associated with plantar fasciitis.

The plantar support assemblies of the present disclosure include a footplate contoured to a portion of a wearer's arch region and an adjustable strap to retain the footplate proximate a wearer's plantar fascia. The footplate includes an undulating profile comprising a medial arch support curve and a lateral arch support curve. The adjustable strap can include a pocket for retaining the footplate and providing additional comfort to the wearer. The footplate is typically designed to deflect a certain degree or distance under compression (e.g., the weight of wearer bears on the arch when walking) and is biased to return to its original shape once the weight has been removed. Rather than absorbing the entirety of a compressive force, the footplate can be designed to deflect upward into the arch to maintain the plantar fascia in a tensioned state.

Plantar support systems of the present disclosure include an adjustable strap and two or more footplate having different hardness or load bearing characteristics.

In one aspect, the present disclosure provides: an assembly for supporting a wearer's plantar fascia, the assembly comprising: a footplate contoured to conform to an arch region of the wearer's foot, the footplate including an undulating profile comprising a medial arch and a lateral arch; an adjustable strap adapted to retain the footplate proximate the arch region during use, wherein the assembly is ambidextrous.

In another aspect, the present disclosure provides, a system for treating plantar fasciitis, the system comprising: an adjustable strap adapted to retain a footplate proximate an arch of a wearer's foot, a first footplate contoured to conform to the arch region of the wearer's foot, the footplate including an undulating profile comprising a medial arch support and a lateral arch support, the first footplate having a first resistance to deflection;

a second footplate contoured to conform to the arch region of the wearer's foot, the footplate including an undulating profile comprising a medial arch support and a lateral arch support, the second footplate having a second resistance to deflection, wherein the first resistance is less than the second resistance.

The terms "comprises" and variations thereof do not have a limiting meaning where these terms appear in the description and claims.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As recited herein, all numbers should be considered modified by the term "about".

As used herein, "a," "an," "the," "at least one," and "one or more" are used interchangeably. Thus, for example, a pressure pad comprising "a" protrusion can be interpreted as a pressure pad comprising "one or more" protrusions.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present disclosure is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exhaustive list.

BRIEF DESCRIPTION OF THE DRAWINGS

The disclosure will be further described with reference to the drawings, wherein corresponding reference characters indicate corresponding parts throughout the several views, and wherein.

Layers in certain depicted embodiments are for illustrative purposes only and are not intended to absolutely define the thickness, relative or otherwise, or the location of any component. While the above-identified figures set forth several embodiments of the invention, other embodiments are also contemplated, as noted in the description. In all cases, this disclosure presents the invention by way of representation and not limitation. It should be understood that numerous other modifications and embodiments can be devised by those skilled in the art, which fall within the scope and spirit of the principles of the invention.

DETAILED DESCRIPTION OF ILLUSTRATIVE EMBODIMENTS

Figure 1:
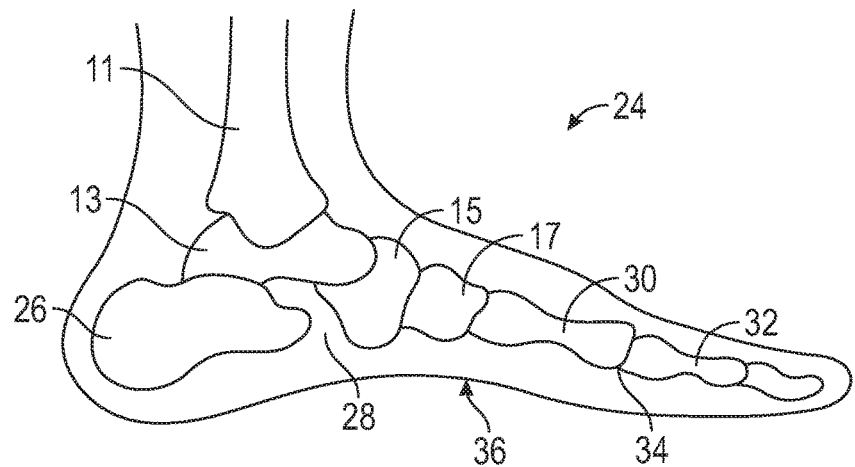
FIG. 1 depicts a schematic of the bones in the human foot.

FIG. 1 diagrammatically illustrates a typical human foot 24 along with the lower end of the tibia 11. This view shows the inside, or medial arch side, of the foot in outline along with an outline of the major bones which would be seen on that side of a skeletal foot. Below the tibia 11 is the talus 13, or "ankle bone". Positioned below and rearwardly of the talus 13 is the calcaneus 26, or "heel bone". Positioned moderately below and forward of the talus 13 is the navicular 15 Immediately behind the navicular 15, and not shown in the illustration of FIG. 1, is the cuboid, which occupies a position similar to that of the navicular 15, but on the outside of the foot. The area between the calcaneus 26 and the navicular 15 and cuboid is the calcaneus-midtarsal connection 28 where the heel meets the arch of the foot 24.

Forward of the navicular 15 and cuboid are the cuneiform bones 17. Extending forwardly from the cuneiform bones 17 are the metatarsals 30 and the phalanges 32. Though not shown, the plantar fascia joins the calcaneus 26 to the MTP joints 34 between the metatarsals 30 and the phalanges 32, generally along the arch 36 of the foot 24.

Figure 2:
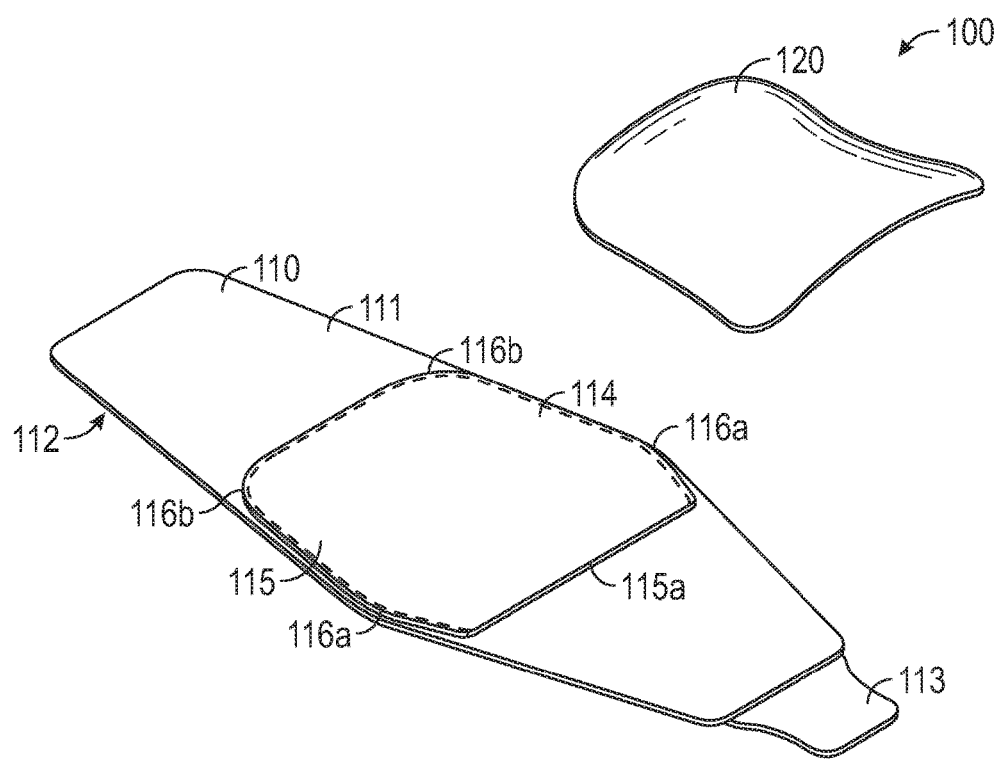
FIG. 2 depicts a perspective view of a plantar support assembly including an adjustable strap and a footplate, according to one implementation of the disclosure.

An exemplary plantar fascia support assembly 100 of the present disclosure is depicted in FIG. 2. The support assembly 100 includes an adjustable strap 110 and a footplate 120. The strap 110 typically comprises a flexible, belt-like apparatus that can be wrapped around the wearer's foot and secured. The strap should be long enough to reach securely around the foot and is preferably wide enough to permit comfortable wear. The width of the strap can help to distribute the applied force along the wearer's arch, so the assembly can held be on firmly but still remain comfortable to the wearer.

In the embodiment shown, the foot strap 110 comprises an elongated piece of flexible, typically elastic material that can be wrapped around the foot to the secure the support assembly thereto. The foot strap 110 is preferably flexible and conformable to improve wearer comfort. The foot strap 110 is typically long enough to wrap around the foot and be secured on the dorsal side thereof (see FIG. 8). In a typical device it will be about 10 to about 15 (25 to 38 cm) inches in length though it will be understood that shorter or longer straps may be used depending upon the size of the wearer's foot. The foot strap is typically wide enough and thick enough to cushion the foot plate 120 on the patient's foot so as to avoid discomfort. In a typical device it will be about 2 to about 3 inches (5 to 8 cm) wide, though foot straps having narrower or wider widths may be used if desired. An illustrative example of a suitable material for use in the foot strap is Hypur-cel® fabric, which is commercially available from Rubberlite, Inc. of Huntington, West Virginia. Additional suitable materials include, but are not limited to, neoprene rubber, silicone rubber, silicone foams, elastomers, thermoplastic elastomers, polymeric materials, urethane foams, polyethylene terephthalate, viscoelastic materials, silicone gel, or any combination thereof. In alternative embodiments, the strap 110 can include relatively inelastic material (for example, a material having no more than about 30% stretch under tension) such as a foam laminate (e.g., a laminate including polyester inner layer, urethane foam, and nylon jersey for exterior durability) or a woven cotton or nylon strap.

The adjustable strap 110 may be secured with any known closure mechanism including but not limited to hook material, mated hook and loop closure (e.g., Velcro® brand systems), adhesive, buckle, snap button, or slot button. As depicted in FIG. 1, the adjustable strap 110 includes a hook material on a closure tab 113 that will releasably engage the outer surface 112 of the adjustable strap 110. Use of a hook material that will releasably engage with the outer surface 112 may be preferred in certain circumstances, as it is easily donned, easily released, and may permit easy adjustment of the support assembly 100 to ensure comfortable, effective wear.

The adjustable strap 110 includes a pocket (i.e., cavity) 115 defined by at least partially by sheet of resilient material 114 disposed on a surface of the strap 110. The pocket 115 may be located on the inner surface 111 of the adjustable strap 110 and include an opening or slit 115a for receiving the footplate 120. The pocket 115 can be formed using various techniques, such as sewing, RF welding, or otherwise securing the resilient material 114 on the adjustable strap 110. In one implementation, the pocket 115 may be defined by an inner surface 111 of the strap 110 and a sheet of resilient material 114 coupled to said inner surface. In another implementation, the pocket 115 may be created prior to attachment, such that the resilient material substantially defines the pocket 115. Suitable resilient materials for use in creating the pocket 115 include a neoprene rubber, a silicone rubber, an elastomer, a thermoplastic elastomer, a polymeric material, a urethane, polyethylene terephthalate, a viscoelastic material, a silicone gel, or any combination thereof. Suitable resilient materials are preferably elastic, breathable, and capable of providing increased comfort to the wearer when the support assembly 100 is retained against an arch.

Figure 6:
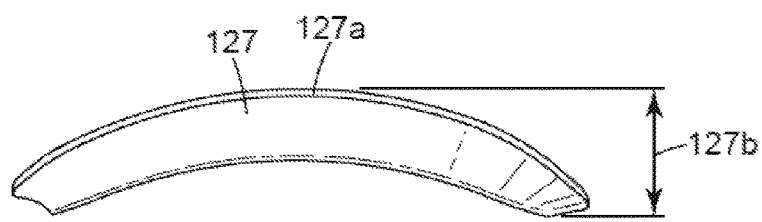
FIG. 6 is the opposite end view of the footplate of FIG. 5.

The pocket 115 is dimensionally adapted to receive and retain one or more footplates 120. As depicted in FIGS. 1 and 6, the pocket includes a geometric profile similar to the footplate 120 and includes medial and lateral contours 116a and 116b. In certain implementations, the opening 115a includes a width less than that of a medial arch support surface of the footplate 120 (see FIG. 4). The relatively smaller opening and a stretchable, elastic material may cooperate to retain the footplate 120 in the pocket 115 without additional closure mechanisms.

In alternative implementations, the adjustable strap 110 includes other retaining structures on a surface thereof, such as clips, rails, and other fastening mechanisms, that fix or substantially fix the footplate 120 relative to the strap 110. In other embodiments, the footplate may be adhered to the adjustable strap or covered by textile material and secured to the strap body by an attachment mechanism, such as Radio Frequency welding (RF Welding), stitching, adhesives, and the like, and combinations thereof.

The adjustable strap may include indicia 244 to assist the wearer in aligning the support assembly 100 relative to the wearer's arch. Suitable indicia can include orientation markings (e.g., arrows), colors, symbols, reference characters, other written designations, and combinations thereof. Indicia may be 10 provided on the inner surface 111 of the strap 110, the pocket 115, or both. For example, the pocket 115 can include an arrow and an "L" to indicate the desired orientation of the assembly when the worn on the left foot.

Figure 3:
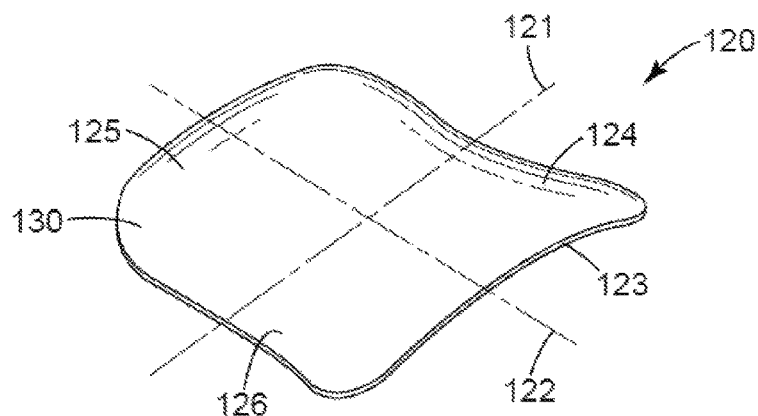
FIG. 3 is a perspective view of the footplate of FIG. 2.
Figure 4:
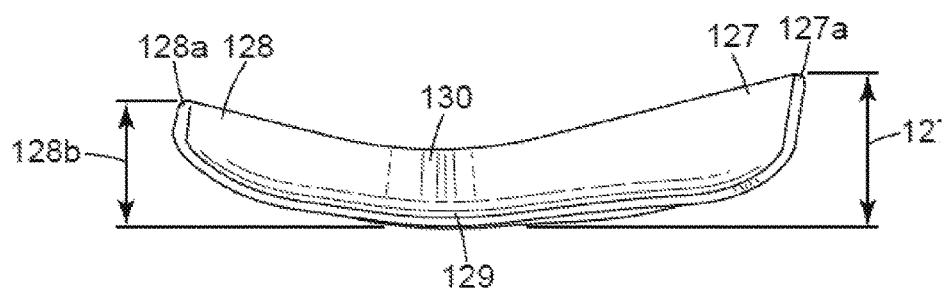
FIG. 4 is a side view of the footplate of FIG. 2.
Figure 5:
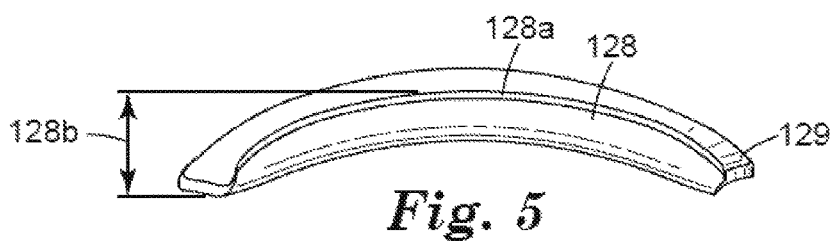
FIG. 5 is an end view of the footplate of FIG. 2.

Turning now to FIGS. 3-5, the footplate 120 of support assembly 100 is designed to contour the curvature of a portion of a wearer's foot, particularly in the arch region. The footplate 120 includes a longitudinal axis 121 and a transverse axis 122, with the longitudinal axis 121 typically intended to substantially align with the longitudinal axis of the foot (i.e., from heel to toe) during use. The footplate 120 includes a medial edge 123, a proximal edge 124, a lateral edge 125, and a distal edge 126 (note that the footplate is ambidextrous and reference to the distal and proximal portions are for illustrative purposes only, as the footplate may be worn on either the right or left arch). The footplate 120 is typically provided pre-shaped (in that includes the undulating, curvilinear profile described below), but can be modified according to certain implementations of the disclosure to more closely contour to the wearer's arch.

The footplate 120 can include an undulating, curvilinear profile adapted to follow the contours of the plantar surface of a wearer's arch. The footplate 120 accordingly includes a medial arch 127 and a lateral arch 128, each design to support the corresponding section of the wearer's arch. In alternative implementations, the footplate can include only one of a lateral and a medial arch, such that the footplate features a single major radius of curvature in the longitudinal direction. In embodiments according to the depicted implementation, both the medial arch 127 and the lateral arch 128 include curvature such that they are convex in profile when viewed along the transverse axis 122 of the footplate 120 (See FIGS. 5 and 6). When placed on the foot according to methods further described herein, the convex curvature allows the arches to at least approximate the natural curvature of a wearer's arch and support the plantar fascia.

The radius of curvature for each arch 127, 128 can vary depending on the potential wearer's anatomical characteristics, but is typically between 3 and 4 inches. In embodiments that include a heat malleable or memory material as described below, the radius of curvature may advantageously change upon application of energy and downward pressure of the wearer's foot to more closely match the curvature of the wearer's arch.

As can be seen with reference to FIG. 4, the medial arch 127 includes a greater height 127b at its peak 127a (i.e., vertex) relative to the footplate base 129, than the vertex height 128b of the lateral arch support 128. The difference in height can contribute to a concave profile for the upper surface 130, when the footplate is viewed along the longitudinal axis 121 (See FIG. 4). The plurality of raised, contoured surfaces provides support for the arches of the foot without collapsing under body weight. Without wishing to be bound by theory, the support curvature on both the medial and lateral sides keeps the plantar fascia in tension (i.e., keeps it from shortening) regardless of attempted flexion or extension, allowing the fascia to properly heal from micro-tears and/or inflammation. Accordingly, the foot assemblies of the present disclosure provide meaningful therapy while a wearer is active and ambulatory.

The footplate 120 is typically thin, so that it maintains a low profile and may be easily inserted into the pocket 114 on adjustable strap 110 or worn with other footwear. The footplate typically has a continuous, generally uniform thickness T of at least 0.025 inches and no greater than 0.1 inches. In some embodiments, the footplate 120 has a thickness T of at least 0.04 inches and no greater than 0.06 inches.

In the embodiment depicted in FIGS. 1-5, the footplate 120 does not include a heel or forefoot portion and is typically dimensioned to fit between the calcaneus 26 and mid-metatarsal 30, while extending from the inner (medial) portion to the outer (lateral) side of the foot. An exemplary footplate 120 has a width 131 of about 2.8 inches and minimum longitudinal length 132 of about 2.8 inches. The exemplary footplate further includes a medial arch support length 133 of about 3.15 inches and a lateral arch support length 134 of about 2.6 inches. It should be appreciated that the above dimensions are provided for illustrative purposes only and are modifiable to account to for different types of arch size, foot width, and other wearer characteristics.

In implementation depicted in FIGS. 1-9, the proximal and distal edges 124,126 generally taper as they approach the lateral arch support edge 125 from the medial support edge 123. This taper can include a curvature, creating a concave profile for the proximal and distal edges 124, 126. The radius of curvature may vary depending upon the wearer's characteristics, but is generally between about 3 and 5 inches. In an exemplary footplate, the proximal edge 124 includes a radius of curvature of about 4.2 inches and the distal edge 126 includes a radius of curvature of 3.4 inches. It should again be appreciated that the above dimensions are provided for illustrative purposes only and are modifiable to account to for different types of arch size, foot width, and other wearer characteristics.

The footplate 120 may include indicia to assist the wearer in aligning the footplate relative to the wearer's arch or the adjustable strap 110. Suitable indicia can include orientation markings (e.g., arrows), colors, symbols, reference characters, other written designations, and combinations thereof. For example, the medial arch can include an arrow and an "L" to indicate the desired orientation of the assembly when the worn on either the left or right foot. As another example, the footplate 120 may be provided with an arrow proximate the lateral arch 128 to indicate the desired orientation of the footplate relative to the pocket 115.

The footplate 120 includes an at least semi-rigid base material, typically a plastic. The base material can comprise a semi-rigid or rigid polymer such as nylon, polyoxymethylene (POM or "acetal"), polyethylene, polypropylene, acrylonitrile butadiene styrene (ABS), polycarbonate, polyamide, or the like. Other suitable base materials include fibrous materials, cork, wood, composites, and metals. In certain implementations, the base material may be heat-malleable. As used herein, a heat-malleable material is a material capable of plastic deformation when heated above a glass transition temperature and compressed by a user's foot. Suitable heat malleable materials include, but are not limited to, polycaprolatone, polylactide, polyethylene terephthalate (PET), polyglycolide, other thermoplastic elastomers (e.g., Hytrel® #2, available from DuPont, Wilmington, Del.), other thermoplastic polymers, copolymers of the aforementioned polymers, or any combination thereof. To avoid injury to the wearer during such deformation, the glass transition temperature of the heat-malleable material is typically between 45 and 75 degrees centigrade.

In certain implementations, the footplate 120 may include a shape memory material. As used herein, a shape memory material is a deformable material capable of returning from a deformed state to an initial shape upon application of an external stimulus or trigger. The trigger is typically a change in temperature, but could also include an exposure to a certain wavelength of light or others means of modifying structural integrity of the material. Particularly suitable shape memory materials include the Essemplex™ and Veriflex™ families of thermoplastic, shape memory polymer resins available from CRG Technologies Inc., of Dayton, Ohio. The use of a shape memory material can extend the useful life of the foot assembly 100, as the footplate 120 can be reused and modified to account for differences in the wearer's right and left arch or differences between users. The shape memory may also allow a wearer to modify treatment during the period of use or correct a fault in the initial deformation.

In certain implementations, the footplate 120 includes a multi-layer construction, with the supporting base material at least partially covered by a soft, flexible material. Suitable materials for the outer layer include thermoplastic elastomers (TPEs), silicone gels and foams, urethane foams, and combinations thereof. The outer material layer can also include a lining or covering made from a heat-malleable material or shape memory polymer. Moreover, the footplate 120 may be formed using different techniques such as injection molding or compression molding or a combination of techniques, such as punching or stamping a composite footplate and bending the footplate surface to a desired curvature.

The footplate 120 is typically designed with a particular resistance to deflection profile, represented by the force needed to displace the center of the footplate a certain distance when the footplate is otherwise fixed. The footplate 120 is also preferably pliable, in that it returns to original shape when applied force is removed. The combination of deflection resistance and the bias toward the original shape can provide near continual support to the plantar fascia. Rather than absorbing the entirety of a compressive force, the footplate can deflect back into the arch to maintain the plantar fascia in a tensioned state. Those skilled in the art will appreciate that the level of resistance can be altered or controlled by, inter alia, material selection, thickness, and manufacturing method. Particularly suitable footplates include a resistance to deflection of at least about 5 to no greater than about 20 pounds of force at a displacement of about 0.25 inches, according to the Resistance to Deflection test method below. In other embodiments, suitable footplates include a resistance to deflection of at least about 10 to no greater than about 15 pounds of force at a displacement of about 0.25 inches, according to the Resistance to Deflection test method below.

Figure 7:
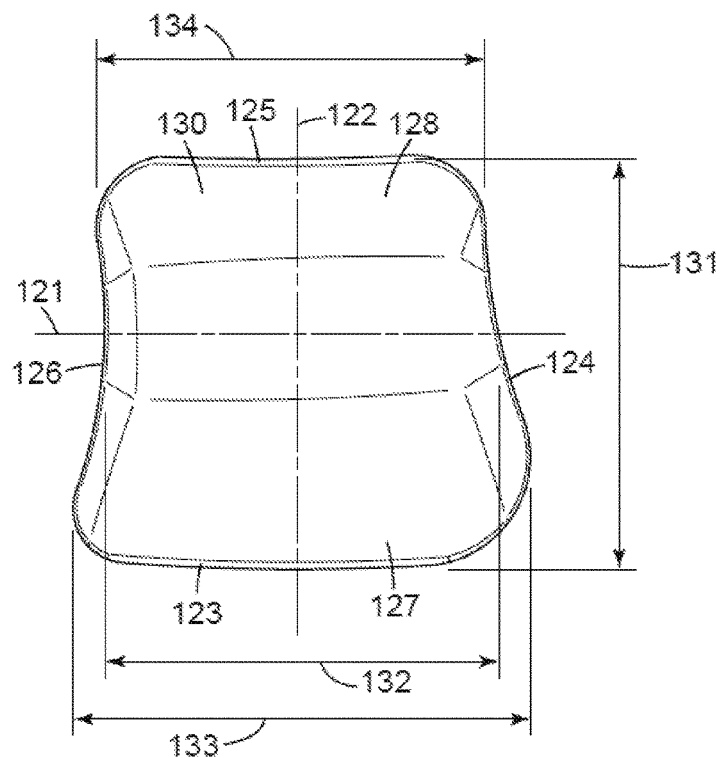
FIG. 7 is a top view of the footplate of FIG. 2.
Figure 8:
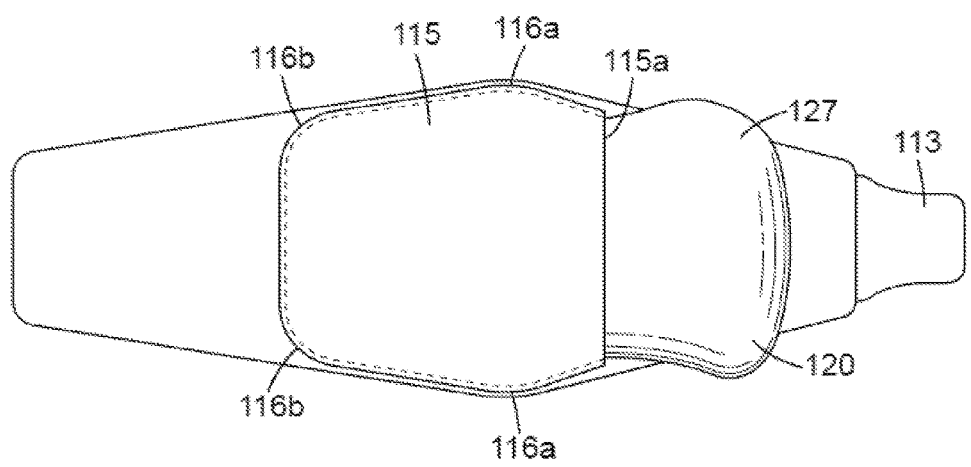
FIG. 8 is a top view of a plantar support assembly prior to retaining a footplate on an adjustable strap.
Figure 9:
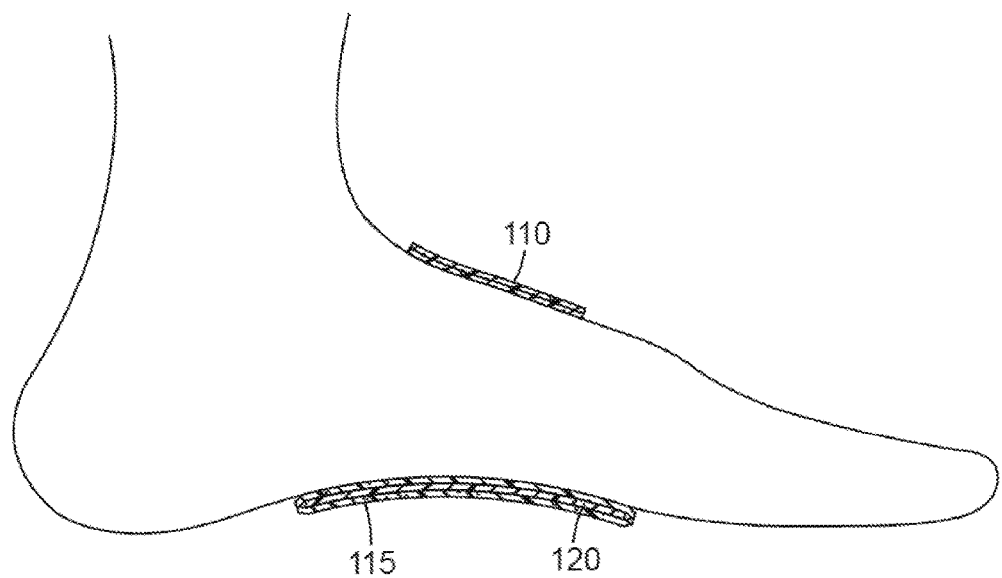
FIG. 9 is a cross-sectional view of the support assembly of FIG. 6 secured to a wearer's foot.

FIGS. 6-8 depict another aspect of the present disclosure: a method for supporting the plantar fascia. In the implantation depicted in FIG. 6, the lateral support edge 125 is positioned relative to the opening 115a and the footplate 120 is inserted into the pocket 115. The footplate 120 is typically inserted until the medial support 127 aligns with the medial contours 116a of the pocket 115 In other implementations, the wearer need not insert the footplate 120, as the plantar support assembly 100 could also be provided preassembled, with the footplate 120 secured to the strap 110.

The longitudinal axis 121 of the footplate is generally aligned with the longitudinal axis of the foot and the medial arch support 127 is positioned relative to the medial arch on either the right of left foot. Once the footplate 120 is secured with respect to the wearer's foot, the adjustable strap 110 is circumferentially wrapped around the foot and then tensioned according to the patient's comfort. The wearer can continue to tighten the strap until the desired support has been obtained. The fastening mechanism (e.g., buckle, Velcro®) can be engaged with the outer surface of the strap after the desired tensioning occurs. The adjustable strap is preferably secured to the dorsal side of a wearer's foot, proximate the navicular and cuboid region, as shown in FIG. 8.

In the event that the footplate includes a heat-malleable and/or shape memory polymer, a practitioner or user of the support assembly may apply a triggering stimulus (e.g., heat) to bring a portion of the material above the glass transition temperature. The heat or other trigger may be applied before or after the footplate 120 is inserted into the adjustable strap 110. Depending on the heat-malleable/shape memory material selected, various triggering apparatuses may be used such as a microwave oven, a convective oven, a hot-air gun, a heating pad, a pan of heated water, a UV light, or any suitable heating unit. The foot may be pressed into the footplate 120 via downward pressure from the user while the footplate 120 remains above the glass transition temperature. Alternatively, the footplate 120 may be pressed against the plantar surface by the user or a practitioner. When subjected to force above the glass transition temperature, the deformable surfaces of the footplate 120 may be plastically deformed into a shape corresponding substantially to the underside of the arch.

The foot may pressed and held into a neutral position by low-Dye or other similar foot taping or strapping techniques, or secured via adjustable strap 110, until the footplate 120 is cooled to a temperature below the glass transition temperature, such as an ambient temperature. The material will then harden and retain a shape that corresponds substantially to the underside of the arch. The result is a customized footplate 120 that can help to keep the user's plantar fascia in tension during ambulation and to provide therapeutic and preventative relief The present disclosure further provides a system for treating plantar fasciitis and other pain associated with the heel and arch. One implementation of a plantar support system 200 includes an adjustable strap 210 and a series of footplates, 220, 230, 240. The support system 200 includes two or more footplates, 220, 230, 240 having different flexibilities and resistance to deflection profiles. In certain preferred embodiments, the system 200 includes three footplates. At least two of the footplates in the series of footplates have a different resistance to deflection profile. In certain circumstances, all of the footplates have a different resistance profile. Accordingly, a user may gradually modify the resistance and support provided by the footplate, progressively increasing or decreasing therapy over time.

Typically, treatment begins with a footplate that is more flexible and provides less resistance to deflection. The user may wearer the first footplate for approximately one week, depending on changes to the plantar fascia. The user may then progress to a footplate having a similar flexibility and resistance profile, though preferably one that is slightly less flexible and more resistant. The user may progressively decrease the flexibility and increase resistance using new footplates until the symptoms desist or the plantar fascia is healed To assist in user compliance, the series of footplates may be color-coded, i.e., presenting a change in color, shade, or gradient indicating an increase in deflection resistance. Different footplates in the series may feature different colors, or the series of footplates may include a changing gradient. In an exemplary system, the footplates include a blue color that grows darker as the deflection resistance increases.

By providing a series of footplates, each offering a similar, but unique resistance profile, the system can offer a broad range of support to the wearer. This in turn offers support to a broader range of foot sizes and characteristics, ensuring adequate therapy. The support system approach also allows individual patients to progressively increase the amount of support offered to meet their personal needs, accounting for the unique challenges of individual feet.

Figure 10:
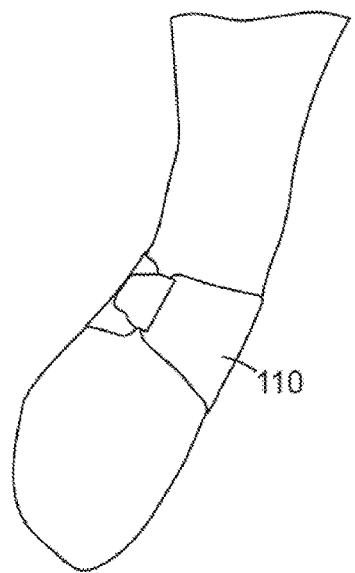
FIG. 10 is a perspective view of the support assembly of FIG. 6 secured to a wearer's foot.
Figure 11:
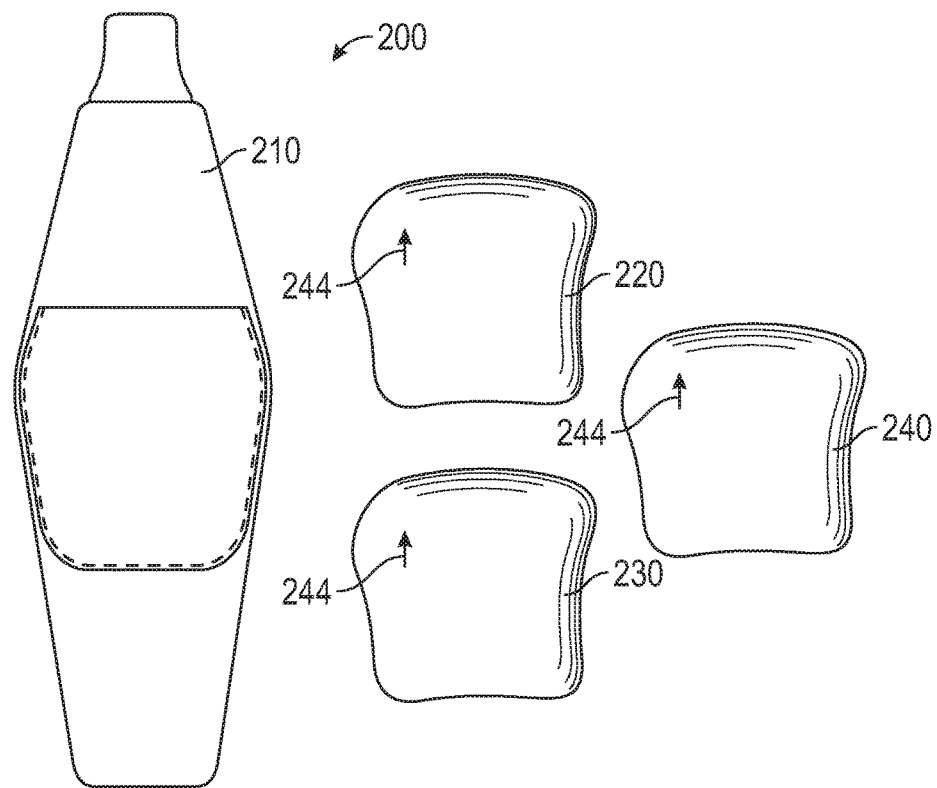
FIG. 11 is a top view of a plantar support assembly according to another aspect of the present disclosure.
Figure 12:
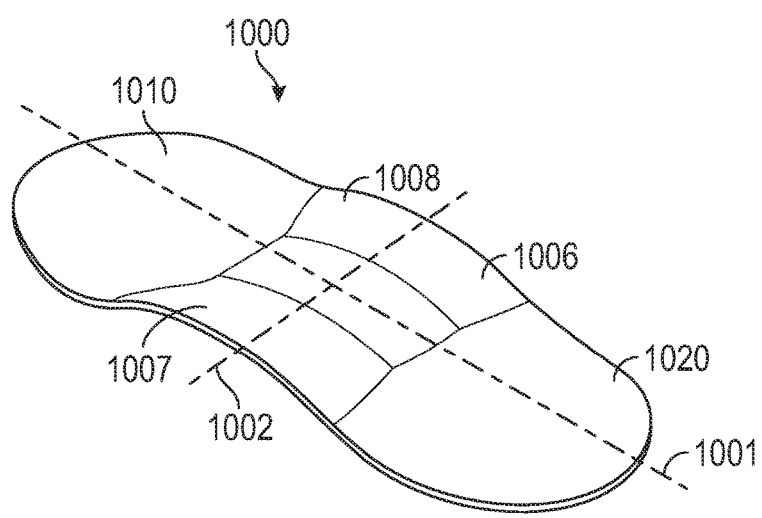
FIG. 12 depicts a perspective view of a footplate according to another embodiment of the invention.

Another embodiment of a footplate according to the present disclosure is depicted in FIG. 10. The footplate 1000 includes a longitudinal axis 1001 and a transverse axis 1002, with the longitudinal axis 1001 typically intended to substantially align with the longitudinal axis of the foot (i.e., from heel to toe) during use. Like the footplate 120, the footplate 1000 is ambidextrous and may be worn on either the right or left arch. Unlike the previous embodiments of footplates, however, the footplate 1000 includes a heel portion 1010 and a forefoot portion 1020. The footplate 1000 is typically provided pre-shaped (in that includes the undulating, curvilinear profile described below), but can be modified according to certain implementations of the disclosure to more closely contour to the wearer's arch.

The footplate 1000 include an undulating, curvilinear profile in the arch region 1006 adapted to follow the contours of the plantar surface of a wearer's arch. The footplate 1000 accordingly includes a medial arch support 1007 and a lateral arch support 1008. Both the medial arch support 1007 and the lateral arch support 1008 include curvature such that they are convex in profile when viewed along the transverse axis 1002 of the footplate 1000. When placed on the foot according to methods described above, the convex curvature allows the arch support surfaces to at least approximate the natural curvature of a wearer's arch and support the plantar fascia.

The footplate 1000 is typically dimensioned to extend from the calcaneus to the mid-metatarsal. The footplate may extend further, but will generally terminate before the toes. The absence to a section supporting the phalanges allows a wearer greater flexion and freedom of movement. The footplate 100 could be used as an orthotic insert and worn inside or outside a wearer's sock. At least one of the upper and lower surfaces may include a removable or repositionable adhesive, such as 3M™9425 Double coated repositionable tape, available from 3M Company, St. Paul, Minn., to retain the footplate 1000 relative to the wearer's foot. The footplate may be adhered to the wearer's sock or the insole of the wearer's shoe. Alternatively, the footplate 1000 may be secured to the foot via elastic or inelastic textile wrap. It should be appreciated that such securement alternatives may be suitable, in certain circumstances, for securing footplate 120 to the wearer's foot.

Embodiments

1. An assembly for supporting a wearer's plantar fascia, the assembly comprising:
   a footplate contoured to conform to an arch region of the wearer's foot, the footplate including an undulating profile comprising a medial arch and a lateral arch;
   an adjustable strap adapted to retain the footplate proximate the arch region during use, wherein the assembly is ambidextrous.
2. The assembly of embodiment 1, and wherein the footplate comprises a heat-malleable material.
3. The assembly of embodiment 1, wherein the footplate comprises a shape-memory material.
4. The assembly of any of the previous embodiments, wherein the footplate has a continuous thickness of at least 0.04 inches and no greater than 0.06 inches.
5. The assembly of any of the previous embodiments, wherein the adjustable strap includes a pocket, and wherein the footplate is retained in the pocket during use.
6. The assembly of any of the previous embodiments, wherein the footplate includes a transverse axis, and wherein the medial arch and the lateral arch include a convex profile when viewed along the transverse axis.
7. The assembly of any of the previous embodiments, wherein the footplate includes a longitudinal axis, and wherein the footplate includes a concave profile when viewed along the longitudinal axis.
8. A system for treating plantar fasciitis, the system comprising:
   an adjustable strap adapted to retain a footplate proximate an arch of a wearer's foot,
   a first footplate contoured to conform to the arch region of the wearer's foot, the footplate including an undulating profile comprising a medial arch and a lateral arch, the first footplate comprises a first resistance to deflection;
   a second footplate contoured to conform to the arch region of the wearer's foot, the footplate including an undulating profile comprising a medial arch and a lateral arch, the second footplate comprising a second resistance to deflection wherein the first resistance is less than the second resistance.
9. The system of embodiment 8, the system including a third footplate having a third resistance to deflection, wherein the third resistance is greater than the first or second resistance.
10. The system of embodiment 8 or 9, wherein each footplate includes indicia on a surface thereof.
11. The system of embodiment 10, wherein the indicia is selected from the group consisting of color, gradient, and orientation markings.
12. A footplate having a longitudinal axis and a transverse axis, wherein the footplate is contoured to conform to an underside of a wearer's foot and includes an undulating profile comprising a medial arch and a lateral arch, and wherein the footplate is ambidextrous.
13. The footplate of embodiment 12, and wherein the footplate comprises a heat-malleable material.
14. The footplate of embodiments 12 or 13, and wherein the footplate comprises a shape-memory material.
15. The foot plate of anyone of embodiments 12-14, and wherein the footplate has a continuous thickness of at least 0.04 inches and no greater than 0.06 inches.
16. A footplate of any of the previous embodiments, and wherein the footplate comprises a plastic.
17. A footplate having a longitudinal axis and a transverse axis, wherein the footplate is contoured to conform to an underside of a wearer's foot and includes an undulating profile comprising a medial arch or a lateral arch, and wherein the footplate is ambidextrous.

Objects and advantages of this disclosure are further illustrated by the following examples, but the particular materials and amounts thereof recited in these examples, as well as other conditions and details, should not be construed to unduly limit this disclosure.

EXAMPLES

Test Methods
Resistance to Deflection

This test provides a means of determining the force (lbf) necessary to displace a formed footplate a specified distance (inches).

The sample footplate is placed in a CHATILLON® TCD225 Series digital force tester (available from Ametek Corporation, Largo, Fla.). Force is applied in a direction generally orthogonal to the center of the sample footplate. The force necessary to displace the sample at certain distance intervals is recorded.

Sample Preparation

Sample footplates were created by the injection molding the particular materials listed in Table I (below) in a mold providing the contours depicted in FIG. 2. Each footplate had a continuous thickness of about 0.04 inches. Three samples of each Example footplate construction (F1, F2, F3, F4, F5) were tested according to the methods above.

TABLE I

| Example | Base Material |
| --- | --- |
| F1 | Globalene HP600S |
| F2 | Globalene ST751 |
| F3 | Nylon 6 |
| F4 | Hytrel ® #2 |
| F5 | Hytrel ® #1 |

Globalene HP600s is a polypropylene homopolymer available from Lee Chang Yung Chemical Industry Corp, Taiwan.

Globalene ST751 is a high impact heterophasic polypropylene (HECO) available from Lee Chang Yung Chemical Industry Corp, Taiwan.

Nylon 6 is a polyamide available from PolyOne Corporation, Avon Lake, Ohio.

Hytrel® #2 is a thermoplastic polyester elastomer available from DuPont™, Wilmington, Del.

Hytrel® #1 is a thermoplastic polyester elastomer available from DuPont™, Wilmington, Del.

Testing results of the Examples are listed in Table II below, with the force necessary to displace a certain distance averaged over the three samples.

TABLE II

| Distance (in) | F1 (polypropylene) Force (lbf) | F2 (Poly Heco) Force (lbf) | F3 (PA6) Force (lbf) | F4 (Hytrel® 2) Force (lbf) | F5 (Hytrel® 1) Force (lbf) |
|---|---|---|---|---|---|
| 0.0625 | 6.17 | 3.98 | 2.54 | 1.66 | 0.88 |
| 0.125 | 12.84 | 8.31 | 5.28 | 3.52 | 1.98 |
| 0.187 | 19.86 | 12.94 | 8.25 | 5.54 | 3.08 |
| 0.25 | 24.51 | 15.57 | 10.68 | 7.08 | 3.79 |
| 0.313 | 24.37 | 15.95 | 10.84 | 7.65 | 4.09 |

Figure 13:
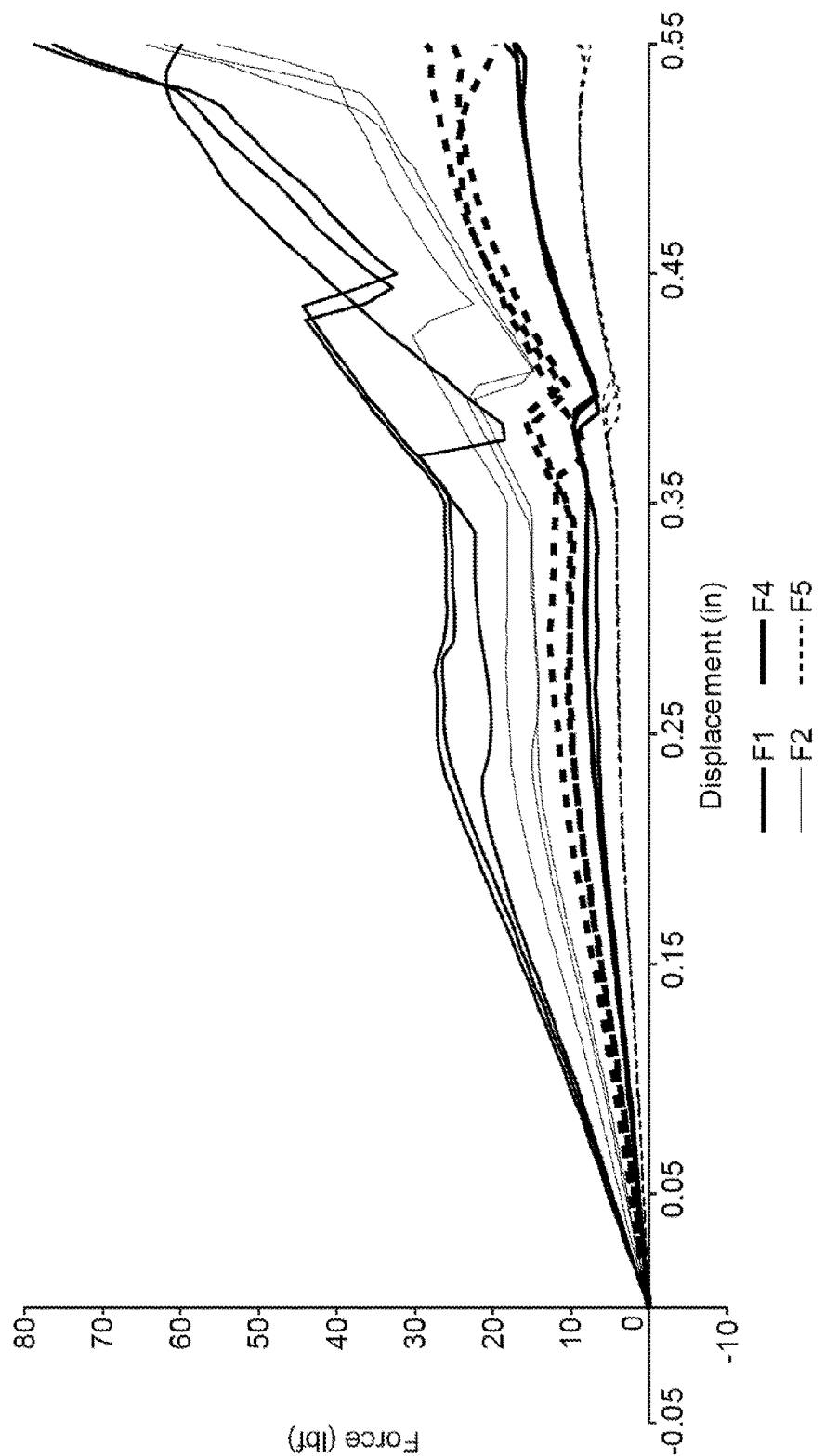
FIG. 13 is a graphical representation of the deflection profiles of various footplate constructions.

The full resistance to deflection profile for each sample tested is depicted in FIG. 13. Though all five footplate constructions where produced in the same tooling, and included the same thickness, each material characteristic offered a unique level of resistive force and linear profile.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

We claim:

1. A system for supporting a wearer's plantar fascia, the system comprising:
   an adjustable strap adapted to retain a footplate proximate an arch of the wearer's foot,
   a first footplate contoured to conform to the arch region of the wearer's foot, the first footplate including an undulating profile comprising a medial arch and a lateral arch, the first footplate comprising a first resistance to deflection;
   a second footplate contoured to conform to the arch region of the wearer's foot, the second footplate including an undulating profile comprising a medial arch and a lateral arch, the second footplate comprising a second resistance to deflection wherein the first resistance is less than the second resistance; and
   wherein each of the first and second footplates has a substantially uniform thickness of at least 0.025 inches and no greater than 0.1 inches.

2. The system of claim 1, the system including a third footplate having a third resistance to deflection, wherein the third resistance is greater than the first or second resistance.

3. The system of claim 1 wherein each footplate includes an indicia on a surface thereof.

4. The system of claim 3, wherein the indicia is selected from the group consisting of color, gradient, and orientation markings.

\* \* \* \* \*

UNITED STATES PATENT AND TRADEMARK OFFICE
CERTIFICATE OF CORRECTION

PATENT NO. : 10,369,038 B2  
APPLICATION NO. : 14/759169  
DATED : August 6, 2019  
INVENTOR(S) : Edward Weaver et al.

Page 1 of 1

It is certified that error appears in the above-identified patent and that said Letters Patent is hereby corrected as shown below:

In the Specification

<u>Column 5</u>  
Line 3, after "15" insert -- . --.

Signed and Sealed this  
Seventh Day of July, 2020

Andrei Iancu  
*Director of the United States Patent and Trademark Office*